United States Patent [19]
Nishihara

[11] Patent Number: 5,990,381
[45] Date of Patent: Nov. 23, 1999

[54] BIOMEDICAL MATERIALS

[75] Inventor: Katsunari Nishihara, Tokyo, Japan

[73] Assignee: ISE International, Co., Ltd., Tokyo, Japan

[21] Appl. No.: 08/968,023

[22] Filed: Nov. 12, 1997

[30] Foreign Application Priority Data

Nov. 13, 1996 [JP] Japan .................................. 8-301759

[51] Int. Cl.⁶ ................................ A61F 2/02; A61F 2/28; A61F 6/14
[52] U.S. Cl. ............................... 623/11; 623/16; 424/422; 424/423
[58] Field of Search ................................ 623/16, 18, 11, 623/66; 424/422, 423

[56] References Cited

U.S. PATENT DOCUMENTS

| | | | |
|---|---|---|---|
| 4,060,081 | 11/1977 | Yannas et al. | 623/11 |
| 4,378,224 | 3/1983 | Nimni et al. | 623/11 |
| 4,623,553 | 11/1986 | Ries et al. | 427/2 |
| 5,071,436 | 12/1991 | Huc et al. | 623/16 |
| 5,211,661 | 5/1993 | Shinjou et al. | 623/16 |
| 5,306,311 | 4/1994 | Stone et al. | 623/18 |
| 5,425,770 | 6/1995 | Piez et al. | 623/16 |
| 5,624,463 | 4/1997 | Stone et al. | 623/18 |
| 5,837,752 | 11/1998 | Shastri et al. | 523/116 |

*Primary Examiner*—Mickey Yu
*Assistant Examiner*—Dinh X. Nguyen
*Attorney, Agent, or Firm*—Fish & Richardson P.C.

[57] ABSTRACT

Disclosed is a biomedical material comprising a shark-derived collagen; a biomedical material comprising a shark-derived collagen and hydroxyapatite; and methods for preparing the same. Since the biomedical materials comprise a shark-derived collagen which is low in antigenicity and high in biocompatibility, they do not cause rejection and they produce effects of good adhesion to organisms and easy remodeling when they are used as artificial skin, artificial tendon, artificial bone, surgical suture or the like. They also have an effect that they do not leave a prominent scar when the wound has been cured. Further, the biomedical materials of the invention are excellent in mechanical strength. Thus, when used as artificial skin, they are hard to tear, good for tightly adhering and capable of following the movement of a joint well.

8 Claims, No Drawings

BIOMEDICAL MATERIALS

1. BACKGROUND OF THE INVENTION

1.1. Field of the Invention

The present invention relates to biomedical materials comprising an extract from Chondrichthyes. More specifically, the present invention relates to biomedical materials using Chondrichthyes-derived collagen which are applicable as various implant materials such as a wound cover, artificial skin, artificial bone, artificial cartilage and artificial tendon, as well as methods for preparing such biomedical materials.

1.2. Description of the Prior Art

When a bone defect has complicated due to some lesion such as an injury, osteoncus or inherent disease, the filling of the defect may be therapeutically necessary. Also, when skin has been damaged by some injury such as a burn, especially when a part of the skin has been lost in full-thickness or almost full-thickness, filling may be necessary.

Conventionally, when filling a bone defect, an autologous bone graft taken from other part of the patient body such as the illium or the fibula has been used if the defect is not so big. When filling a big bone defect in the skeletal system, an artificial bone has been prepared using a ceramic of metals such as titanium, alumina and zirconia or oxides thereof, a ceramic such as apatite and a composite material of these substances to thereby supplement the defect.

When filling a skin defect, a non-bioabsorbable or bioabsorbable, sheet-type wound cover or artificial skin has been used. The term "wound cover" used herein means a material which merely covers the site of skin defect physically, and the term "artificial skin" used herein means a substitute skin which has the possibility of taking the place of skin grafting.

As a non-bioabsorbable thin sheet-type wound cover, a thin, elastic, synthetic polymer sheet made from polyurethane, silicone or the like may be given. As an bioabsorbable wound cover, freeze-dried porcine corium, a sheet made of chitin, collagen, alginic acid and the like are known. In addition to these sheet-type wound covers, powder of a cellulose derivative is also known which is applied to the injured site to form a sheet thereon. As artificial skin, one composed of cell-free materials and a cultured skin which is obtained by two-dimensionally culturing human epidermal cells are known. As a material for the former artificial skin, spongy collagen is known.

Those materials used for the above-mentioned purposes are required, from the viewpoint of organisms, to manifest positive functions and yet to fit compatibly with organisms (i.e., to have biocompatibility). Biocompatibility can be roughly divided into histocompatibility and blood compatibility. When a material of low biocompatibility is embedded in or contacted with an organism, components eluted from the material or worn out pieces of the material separated from its surface penetrate into the tissue surrounding the material or spread in the organism through blood circulation to cause a systemic tissue reaction, which results in various problems such as necrosis of a tissue. On the other hand, from the viewpoint of material itself, the above-mentioned materials are required not to deteriorate upon contact with organisms and to maintain for a specific period of time physical and chemical properties that could satisfy a required function.

Further, these materials should not differ greatly in mechanical properties from the tissues of organisms to which they are to be jointed. In other words, these materials need to have mechanical biocompatibility. This is to prevent the occurrence of incompatible distortion or stress concentration on or near the junction which may cause breakage or abnormality at the junction and thus make it impossible for the jointed material to manifest the function of interest.

These materials are further required to be capable of perfect sterilization and disinfection and to be capable of standing these treatments.

However, conventional materials described above have been pointed out to have several problems. For example, since metals are extremely high in strength, they are indispensable as a substitute skeleton which effects biofunctions. However, when a metal is used in filling a bone defect, an organism does not recognize the metal as a part of the self and, thus, a problem will occur in a long-term use. Even if the metal has been coated with a ceramic which is well biocompatible with the organism, there is a drawback that the ceramic will be shed from the metal during the course of use. Thus, this technique has not been put to practical use.

Collagen is mainly used in wound covers and artificial skin and such collagen is derived from bovine. It is known that bovine-derived collagen has antigenicity. Thus, it is necessary to carry out a special treatment or use fetal collagen without antigenicity.

There are blood groups in human blood and major histocompatibility antigens in human tissues. It is well known that a transfusion of blood not matching the blood group of a patient induces rejection that may eventually kill the patient. As such blood groups, the ABO system, the Rh system, the Ii system, the P system, the MN system and other blood groups are known. Accordingly, when a blood transfusion, bone marrow transplantation, organ transplantation from a living donor, or tissue transplantation from a living donor is to be performed, selection of a donor compatible with the patient in blood group is very critical for making the transfusion or transplantation. successful, though it is difficult to find out a completely matching donner for individual patients.

Such a problem is also encountered similarly in implant materials which are used to be implanted in a tissue successfully or for regenerating a tissue or for other purposes. Therefore, even in the case where the use of an organism-derived material is expected to produce desirable results, incompatibility in blood group cannot be avoided and causes the problem of rejection at the time of take or regeneration of the tissue. The term "implant" used herein means an artificial device embedded or transplanted into the body for medical purposes.

Further, the bovine-derived collagen described above has a problem that it is slightly weak in mechanical strength when shaped into a sheet or film and easy to break when used in a narrow width. When this collagen is used in artificial bone or artificial skin, it has a problem of fragility in addition to the above-described problem of biocompatibility.

2. OBJECTS AND SUMMARY OF THE INVENTION

Toward the solution of the problems described above, the inventors of the present invention have made intensive and extensive researches from a phylogenetic viewpoint. As a result, it has been confirmed through a phylogenetic study that the blood group substances and the histocompatibility antigens described above came into existence at a specific stage of the evolutional process. Then, the inventors have actually made tissue transplantation experiments using those animals representing various evolutional stages and examined whether rejection for the transplanted graft occurs or not. As a result, it has been found that transplantation of an extract from a tissue of Chondrichthyes or a tissue itself of Chondrichthyes would not cause such rejection and that the extract from them are stronger. Thus, the present invention has been achieved.

The present invention relates to biomedical materials comprising an extract or an extirpated piece from a tissue of Chondrichthyes. Specifically, the extract may be collagen and the extirpated piece may be skin, muscular tissue or cartilage. The biomedical materials of the invention may further comprise hydroxyapatite. The biomedical materials of the invention may further comprise one or more compounds selected from the group consisting of hyaluronic acid, chondroitin sulfate, amino acids and nucleic acids.

The present invention also relates to a method for producing the biomedical materials described above comprising shaping an extract from a tissue of Chondrichthyes into a sheet, film or yarn.

The present invention further relates to a method for producing the biomedical materials described above comprising mixing an extract from a tissue of Chondrichthyes and hydroxyapatite and sintering the mixture at a low temperature.

3. DETAILED DESCRIPTION OF THE INVENTION

As the Chondrichthyes to be used for obtaining an extract or extirpated piece for preparing the biomedical materials of the invention, fishes belonging to Elasmobranchii which includes a number of sharks, rays, and skates are preferable. Among all, sharks are most preferable. Specific examples of sharks include dog shark, spotted shark, dochizame and nekozame. Specific examples of rays are stingray and sawfish.

Specifically, the extract obtained from these Chondrichthyes is collagen. Collagen is a peculiar fibrous protein found in every multicellular animal. Collagen is found most abundantly in mammals, amounting to 25% of the total protein. To date, seven genetically distinguishable collagen a chains have been known, and type I, type II, type II, type IV and type V collagens are known. Collagen may be obtained by extracting from various tissues. For example, when extracting collagen from such as skin, tendon or ligament, extraction is performed with acid and the extract is desalted to obtain a liquid collagen. When collagen is extracted from bone or ebur dentis, such a material is crushed and dealcified with EDTA (ethylenediaminetetraacetic acid). The resultant insoluble collagen is suspended in a buffer and desalted by a combination of, for example, heating treatment and enzyme digestion to thereby obtain a liquid collagen. Hereinafter, the collagen thus obtained from sharks is called a shark-derived collagen and the collagen thus obtained from rays is called a ray-derived collagen.

Specifically, the extirpated piece from these Chondrichthyes is skin, muscular or cartilage tissue. Any piece of the skin tissue extirpated from the Chondrichthtes' body may be employed in the present invention, preferably the skin tissues from dorsum to abdomen, because a large piece of the tissue is obtained. Skin composed of epidermis, corium, and tera subcutanea, and tera subcutanea is preferably employed from the view point of transplantation techniques and postoperative control for patients. Hereinafter, tera subcutanea is defined as the fibrous tela of which upper face connected to corium with reticule structure, in which rough connective tissue and/or muscle tissue, and connected to fascia through its lower face.

Any piece of the muscle tissue extirpated from the Chondrichthtes' body may be employed in the present invention, preferably the skin tissues from dorsum to abdomen, because a large piece of the tissue is obtained.

The skin or muscle tissue obtained from Chondrichthtes is washed with an large amount of sterilized saline, and is immersed into the saline containing antibiotics before use. Any generation or kind of antibiotics may be employed in the present invention when it is for injection. Specific examples of such antibiotics are Shiomarin, Streptomycin, Cefotaxime, Ceftizoxime, Cefmenoxime, and Cefoperazone.

The cartilage obtained from any endoskeleton and/or condrocranium may be employed, and preferably spinal column, in the view point of the size of extirpated tissues or easiness of processing the extirpated tissue.

The extract or extirpated piece from these Chondrichthyes is preferable because there exists no blood group substance or major histocompatibility antigen (i.e., no antigenicity) in the extract (collagen) or the extirpated piece (skin or muscular tissue) from sharks or rays which are known as representatives of ancient organisms living now. Furthermore, since collagen is present almost in the form of monomer in the fins and the cartilage of sharks and rays, such collagen is easily to be purified, and collagen can be also obtained easily from their skin and teeth by decalcifying.

Specific examples of the biomedical materials of the invention include wound covers, artificial skin, artificial bone, artificial cartilage, artificial tendon and surgical suture.

A wound cover is a thin sheet-like material which is used to block bacteria invasion from the outside to thereby prevent infections and to inhibit the evaporation of moisture from the inside to thereby prevent dehydration. Wound covers are classified roughly into non-bioabsorbable type and bioabsorbable type. A bioabsorbable wound cover melts as it absorbes effusion, while the shape of a non-bioabsorbable one remains unchanged permanently.

Artificial skin is used for a severe skin defect of second- or third-degree due to a burn or the like. Artificial skin is classified into two types; one which is composed of human dermal cell free materials and the other one called "cultured skin" which is obtained by two-dimensionally culturing human dermal cells. The wound cover and/or artificial skin of the present invention may be produced by mixing collagen extracted from Chondrichthtes and other materials. Specific examples of the materials are chitin, chitosan and other suitable polymers. When the wound cover and/or artificial skin is produced from collagen and other materials, it may be shaped into various form such as a flat membrane and a spongy layer to use distinctively depending on conditions or sites of damages. Alternatively, the skin tissues are extirpated from the shark, and the epidermis is removed by a sand paper with suitable roughness or a knife to treat an inorganic acid to remove the rough connective tissue to obtain artificial skin. The specific examples of the inorganic acids are HCl and hypochlorite. Since the biomedical materials of the invention comprise Chondrichthyes-derived collagen having no antigenicity, when they are used as an bioabsorbable wound cover or the former type artificial skin, they have advantages that successful take or implantation can be achieved and that a scar will not be prominent when the wound has been cured.

Artificial bone is a material which mainly effects as a substitute for bone the functions of load support, load transfer and shape maintenance among the functions of bone. Bone tissue plays two roles; one is to construct and maintain a body structure and the other is to store calcium in calcium metabolism. Bone is composed of cells and osteoid, the cells being divided into osteroblasts producing osteoid and osteroclasts resorbing osteoid. As a result of the functions of these two types of cells, formation and resorption called "remodelling" is always effected in bone.

Osteoid is composed of organic components amounting to 20% in the total weight and inorganic components amounting to 80% of the total weight. Ninety percent of these organic components is type I collagen and the major inorganic component is hydroxyapatite. Accordingly, it is preferred that a highly biocompatible artificial bone be composed of collagen and hydroxyapatite. Further, since bone has the functions of load support, load transfer, etc. as described above, artificial bone should have a sufficient strength to stand such loads. In addition, since artificial bone is grafted in the body to use for a long period of time, it is necessary to use a collagen with no antigenicity.

Hydroxyapatite expressed by the formula $Ca_{10}(PO_4)_6(OH)_2$ is one of the representative calcium phosphate ceramics and is the major constituent mineral in bone and teeth.

Hydroxyapatite is the major component in those minerals constituting teeth and bone and excellent in biocompatibility with tissues. Hydroxyapatite has been already commercialized as a bone filler and a bone-replacing material. Although sintered hydroxyapatite is superior to bone in compression strength and bending strength. Although the compression strength, bending strength, Young's modulus, etc. of a sintered hydroxyapatite vary depending on the treatment conditions, generally, very high values of about 900 $kg/cm^2$ in compression strength and more than 700 $kg/cm^2$ in bending strength are obtained. However, it has a disadvantage of being weak against impact.

Hydroxyapatite may be synthesized, for example, by the wet method in which calcium ions and phosphate ions are reacted in an aqueous solution at 100° C. or below; by the dry method in which calcium and phosphoric acid are reacted on a solid phase at a high temperature around 1000° C. in air or under a steam atmosphere; and by the hydrothermal method in which the synthesis is performed using an aqueous solution reaction at a high temperature under a high pressure in an autoclave. Synthesized hydroxyapatite may be variously shaped using a metal mold, rubber or the like. As a biomaterial, hydroxyapatite may take the form of a tight material, granules, powder or a porous material.

The biomedical materials of the invention comprise hydroxyapatite and a collagen derived from Chondrichthyes having no antigenicity. In order to confer strength on an artificial bone, hydroxyapatite and collagen need to be sintered. However, since collagen does not remain under standard sintering conditions (around 1000° C.), it is necessary to sinter them at a low temperature as described later. The artificial bone of the invention sintered at a low temperature has sufficient strength in load supporting, etc. and it does not cause inflammation or the like even if it has been embedded for a long time since it has no antigenicity. Artificial cartilage is a substitute for cartilage which is a support organ composed of cartilage tissue. Cartilage is well developed in vertebrates and generally found in a part of the skeletal of an organism, walls of tubular organs such as the respiratory tract, surfaces of joints that undergo friction, and the like. Cartilage tissue is one of fibrous connective tissues composed of cartilage cells and cartilage matrix. In cartilage matrix, collagen amounts to 50–60% and glycosaminoglycans such as hyaluronic acid and chondroitin sulfate are also contained.

The hydroxyapatite-collagen composite of the invention for use as a biomedical material is preferably a powder form, sheet form or porous form from the viewpoint of shaping and handling. The particle size of this hydroxyapatite powder is not particularly limited as long as a sintered product can be prepared with jigs such as a metal mold and rubber. Preferably, the size is several micrometers or less. As a hydroxyapatite monomer, such as APASERAMU (from Asahi Chemical Industry) may be given.

The artificial cartilage of the invention preferably comprises one or more components selected from hyaluronic acid, chondroitin sulfate, various nucleic acids and various amino acids, in addition to the collagen and hydroxyapatite described above.

As the artificial cartilage of the present invention, the extirpated from the above-mentioned Chondrichthtes may be employed, and the synthetic ones by sintering hydroxyapatite and other components such as collagen may be used. For example, when the extirpated is used, the spinal column is extirpated from Chondrichthtes. Then is shaped into a cube or pararellepipedon by using the knife, or a column by using a trephine. Alternatively, the artificial cartilage is produced by using collagen, hydroxyapatite, and the above-mentioned other component as described below. Specific examples of the other components are hyaluronic acid, chondroitin sulfate, nucleic acids, and amino acids. When the artificial cartilage of the present invention contains at least one component described above, its biocompatibility and lublicity are both improved.

Hyaluronic acid is one of glycosaminoglycans made up of repetitive disaccharide units of O-β-D-glucuronosyl(1→3)-N-acetyl-D-glycosaminyl(1→4). Hyaluronic acid has a property of binding to a large quantity of water to form a gel and thus is necessary to allow joints to move smoothly. The hyaluronic acid used in the invention may be a commercial hyaluronic acid.

Chondroitin sulfate is one of glycosaminoglycans distributed in cartilage and other connective tissues of animals in general, and supports the elasticity and tensile strength of the tissues. In addition to a chondroitin sulfate comprising O-β-D-glucuronosyl(1→3)-N-acetyl-D-galactosamine-4-sulfate units, one having a sulfate group at position 6 of N-acetylgalactosamine; one comprising N-acetylgalactosamine-4,6-disulfate; one comprising glucuronic acid-2(or 3)-sulfate; and the like may be used.

The term "nucleic acid" used herein means single- or double-stranded DNA or RNA. These nucleic acids may be either circular or linear, and their lengths are not particularly limited.

The term "amino acids" include, in addition to essential amino acids, aminoadipic acid, aminocaproic acid, ethylglycine, methylvaline, ornithine and other modified amino acids, and those amino acids which are not contained in ordinary proteins. With respect to these nucleic acids and amino acids, commercial products from Sigma, for example, may be used.

If one or more of these components are contained, it is preferable in preparing an artificial bone, artificial cartilage or chamber which is excellent in tensile strength and elasticity. The term "chamber" used herein means an in vivo tissue culture vessel made of artificial cartilage and artificial bone in which the environment of a living body is provided and which has an action of allowing a tissue to be bioavailable. Each of the components enumerated above is most appropriate for the preparation of a highly biocompatible artificial bone or artificial cartilage when contained at a ratio of about 5–10% relative to the weight of the hydroxyapatite used.

When the artificial skin or surgical suture of the invention comprising Chondrichthyes-derived collagen is prepared, it is preferred that such biomedical materials be impregnated with antimicrobial agents and antibiotics in addition to the components described above. By allowing them to contain those agents, biomedical materials with antimicrobial effect can be obtained. As antimicrobial agents, any conventional antimicrobial agents may used freely. Specifically, sulfa-type antimicrobial agents such as silver sulfadiazine, zinc sulfadiazine and cerium sulfadiazine; aminoglycoside type antimicrobial agents such as gentamycin sulfate, streptomycin sulfate and fradiomycin sulfate; penicillin type antibiotics such as ampicillin and sodium methicillin; and the like may be used.

In the preparation of the wound cover and/or artificial skin of the invention, a mixture of Chondrichthyes-derived collagen and other components may be shaped into a flat membrane or a spongy layer. Alternatively, a layer containing the above collagen may be laid upon another layer containing other components. As other components, polysaccharides such as chitin and chitosan; polymer materials such as polyurethane; and the like may be enumerated.

When the skin tissue of Chondrichthtes is used as the wound cover or artificial skin of the present invention, the epidermis is removed from the extirpated tissue to treat with an acid to make spongy rough connective tissue, as described above. Alternatively, the wound cover and/or artificial skin may be laid with some other components, for example, chitin, chitosan, and polyurethane.

The wound cover and/or artificial skin of the invention is placed upon a site of tissue defect. The artificial skin of the invention is for tightly adhering to the site of wound. Even when applied to a wound at a joint, the artificial skin of the invention sufficiently follow the movement of the joint. When applied to a wound with much effusion (e.g., a burn), the artificial skin of the invention has an advantage that, if small pores have been provided in the artificial skin in advance, moisture permeability is secured without remarkable decrease in mechanical strength and thus effusion does not stagnate between the wounded site and the artificial skin.

The wound cover or artificial skin of the invention comprising Chondrichthyes-derived collagen is prepared, for example, as described below.

Collagen is extracted and purified from fins of a shark by conventional methods. The resultant collagen is made into a solution, which is appropriately mixed with desired components as described above and diluted. Then, the resultant solution is transferred to a vessel of an appropriate size and freeze-dried to obtain a sponge. The size or thickness of this sponge is not particularly limited. Its size is preferably 10×10 cm or less, more preferably about 5×5 cm, 5×2 cm or 2×1 cm, in view of easiness in handling and storage. Its thickness is preferably 1 mm or less. When the thickness is about 0.5 mm, the wound cover or artificial skin applied to a movable portion of the body such as a joint has an advantage that it adheres to the site closely and follows the movement of the joint well.

The wound cover or artificial skin of the present invention comprising the skin tissue or fin extirpated from Chondrichthtes is prepared, for example, as described below.

The skin tissue with rough connective tissue is extirpated from the skin of Chondrichthtes, for example, the shark, with a cutting tool such as a saw. Then, the hard epidermis of the extirpated tissue is removed by using the sand paper with suitable No. or the knife. The resultant tissue is treated with an inorganic acid such as hypochloride in suitable concentration to form the spongy layer for the wound cover and/or artificial skin. The size or thickness of this sponge is not particularly limited. Its size is preferably 10×10 cm or less, more preferably about 5×5 cm, 5×2 cm or 2×1 cm, in view of easiness in handling and storage. Its thickness is preferably 1 mm or less. When the thickness is about 0.5 mm, the wound cover or artificial skin applied to a movable portion of the body such as a joint has the advantage that it adheres to the site closely and follows the movement of the joint well.

It is also possible to prepare a surgical suture by preparing fiber from the collagen described above and twisting up the fiber. Alternatively, the fiber in the form of monofilament may be used as a surgical suture.

The fiber prepared from the collagen may be braided or woven into a ribbon and used as an artificial ligament or tendon. The thickness of the fiber to be prepared may be appropriately decided depending on its use and is not particularly limited. If the fiber is for use as an artificial ligament or tendon, bundles of fiber 100 $\mu$m of less, preferably about 60 $\mu$m in thickness are braided to prepare a braide.

The wound cover or artificial skin of the present invention comprising the tendon or muscle tissue extirpated from Chondrichthtes is prepared, for example, as described below.

In the preparation for the artificial tendon, for example, the tendon The skin is extirpated from the basal part of fin of Chondrichthtes, for example, with the cutting tool such as the saw. Then, the extirpated tissue is removed by using the sand paper with suitable No. or the knife. The resultant tissue is shaped into a piece with the size of 2×5 cm or less to use the artificial tendon.

In the preparation for the artificial muscle, the extirpated muscle tissue is similarly treated. When the size larger than 2×5 cm causes troubles for application into the larger wound site, the tissue size is preferably 2×5 cm or less. When the artificial tendon or muscle is applied on the wound site, they may be shaped into suitable size or form by using the cutting tool such as the knife.

Once applied, the thus prepared artificial skin, artificial ligament and artificial tendon become rapidly united with tissues of the patient and do not leave a prominent scar because Chondrichthyes-derived collagen, the major component of these biomedical materials, is low in antigenicity.

In the preparation of an artificial bone or artificial cartilage, the above-mentioned collagen solution is mixed with the hydroxyapatite described above at a desired mixing ratio and then sintered at the low temperature with high pressure described above. The concentration of the collagen solution described above is about 1 to 5 % (w/v), preferably about 2%. The particle size of hydroxyapatite is about some $\mu$m or less, and Apaseram described above may be preferably used.

The collagen solution is diluted by about 5 to about 30 times, preferably about a dozen times, and then mixed with 0.5 to 1 M of phosphate solution to obtain collagen-phosphate solution. Calcium hydroxide solution is prepared to mix with the collagen-phosphate solution to obtain the aqueous solution, and then the solution is mixed with hydroxyapatite to form precipitate. The mixing ratio (w/v) of the above collagen solution to the ultrafine hydroxyapatite powder is preferably from 0.1:9.9 to 2.0:8.0. When this ratio is 1.0:9.0, the material achieves an effect that compression strength and bending strength are high and yet fragility is small.

The water contents in the precipitate formed is reduced with a suitable device, for example, a lyophilizer, and then is packed into a suitable wear to obtain the artificial bone by sintering. The artificial bone is produced by sintering at ultra high-pressure with low temperature in the presence of water. Specifically, the sintering process is performed at several thousands atoms with the temperature between about 35 to about 45° C. in the presence of water for several hours to a dozen hours. Preferably, this sintering is done at 2,000 atoms, about 40° C., for about 8 hours. When the artificial bone is produced under such conditions, it has large strength without any denaturation of collagen.

Small pieces are shaped by various shaping methods using a metal mold, rubber, hot pressing, etc. For example, when a metal mold is used, a mixture of the above-mentioned mixing ratio is placed in the mold and sintered under an ultrahigh pressure at a low temperature in the presence of water.

Such a sintered material may be either tight or porous. The size and shape of this sintered material are appropriately selected depending on the site of application. For example, when the sintered material is to be applied for filling a bone defect, a rectangular parallepiped or a cube about 4×3×3 cm, 3×2×2 cm, 1×1×1 cm, 0.5×0.5×0.5 cm or 1×1×0.3 cm in size is prepared.

Alternatively, the artificial cartilage with lublicity is obtained by adding at least one component selected form other components such as amino acids, hyaluronic acid, chondroitin sulfate when the artificial bone is produced.

When the extirpated spinal column is used, the column is shaped into a block with rectangular or circular section by using the knife or trephine to obtain the artificial cartilage of the present invention. The shaped cartilage is then washed in the large amount of sterilized saline. The size of the cartilage is preferably 2×5 cm or less in the view point of implant technique and good taking of the graft after transplantation.

When the thus prepared piece is embedded in a site of bone defect, a good adhesion to the organism is achieved and the piece readily undergoes remodeling because such artificial bone is low in antigenicity like the artificial skin described above. Consequently, the time required for the embedded bone to be reabsorbed and replaced with the newly formed, organism-derived bone and cartilage connective tissue is short. Since the embedded bone is thus replaced with the organism-derived bone and cartilage connective tissue, the artificial bone or the like of the invention has an advantage that it does not cause necrosis of the peripheral tissue.

Further, the artificial skin, tendon, bone cartilage or bone of the invention comprising a shark-derived collagen can be sterilized after shaping with radiation or an ultrahigh pressure and can be stored aseptically at a low temperature. From these viewpoints also, the materials of the invention are suitable as biomedical materials.

Specifically, the biomedical materials, which comprising collagen derived from Chondrichthtes, of the present invention may be stored in saline for about 6 month at about −60° C.

Accordingly, many sheets of the biomedical materials of the present invention is required urgently, the invention may respond to such requirements.

PREFERRED EMBODIMENTS OF THE INVENTION

Hereinbelow, the present invention will be described more specifically with reference to the following Examples, which are not intended to limit the scope of the present invention.

EXAMPLE 1
Rejection in Grafting using Shark derma

One nekozame 60 cm in body length and three dochizamees 100 cm in body length were used. The sharks were anesthetized by adding p-aminobenzoic acid to the sea water in which they were kept to give a concentration of 100 ppm. A piece of the dorsal skin 2×2 cm together with placoid scales was extirpated from each shark. The extirpated piece from the nekozame was grafted to one dochizame, and the extirpated piece from this dochizame was then grafted to the nekozame. Also, allografting was performed between the two remaining dochizamees. As a control, a dochizame was used. A piece of skin 2×2 cm together with placoid scales was extirpated from this fish in the same manner as described above and this piece was returned to the operation site.

In both heterografting and allografting, each skin graft was implanted successfully in two weeks after the operation without causing rejection. Three months thereafter, re-grafting was performed between the two dochizamees which had undergone allografting. This re-grafting was successful without any particular problem.

The graft from the nekozame and the area surrounding it were completely covered with placoid scales of the recipient dochizame. The results are shown in Table 1.

TABLE 1

| Type of Grafting | Graft | Recipient | Presence or Absence of Rejection | Successful Implantation Ratio (%) |
| --- | --- | --- | --- | --- |
| Heterografting | Skin from dochizame | Nekozame | None | 100 |
| Allografting | Skin from dochizame | Dochizame | None | 100 |

As shown in Table 1, in both allografting and heterografting between sharks of different spiecies, grafting with shark skin did not cause rejection. Furthermore, neither inflammation at the operation site nor separation of the graft was observed.

EXAMPLE 2
Rejection in Transplantation using Shark Muscle

From one of the dochizamees used in Example 1, a piece of muscle 5×5×8 mm was extirpated. On the other hand, a portion of muscle was extirpated from the dorsal muscle and the femoral muscle, respectively, of a frog (Xenopus ; body weight: 30 g) and the extirpated piece from the dochizame was transplanted to the resultant vacancy.

No rejection or necrosis was observed 24 hours, 48 hours, 96 hours, 14 days and 2 months after the transplantation.

Since such rejection or inflammation results from the involvement of blood group substances and histocompatibility antigens, it has been shown that these substances and antigens are not present in sharks.

EXAMPLE 3
Rejection of the Shark-Derived Collagen

A spongy sheet lyophilized from the collagen solution obtained from the group consisting of fresh skin, cartilages, by using conventional method, and fins was grafted on the dorsal muscle of dogs (adult; male; 30 kg).

The sheet was extirpated 24 hours, 48 hours, 96 hours, 14 days and 3 months after the operation and observed histopathologically. As a result, no inflammation was induced.

From the above, it has become clear that collagen derived from sharks, like fetal proteins, does not manifest antigenicity even when administered to a heterologous animal. In other words, it has been suggested that no blood group substance or the like is present collagen derived from sharks.

EXAMPLE 4

Preparation of an Artificial Bone

The collagen concentration in the collagen solution obtained in Example 3 was adjusted to 2%. Five hundred milliliters of the resultant collagen solution was diluted to 8 liters and mixed with 0.6 mole of phosphoric acid to thereby prepare a mixed solution of collagen and phosphoric acid.

One mole of calcium carbonate ($CaCO_3$) was kept at 900° C. in air for 10 hours. The thus formed calcium oxide (CaO) was crushed in a mortar to obtain fine powder, which was mixed with 3 liters of water to produce an aqueous calcium hydroxide ($Ca(OH)_2$) solution. This aqueous $Ca(OH)_2$ solution was agitated vigorously and the collagen-phosphoric acid mixed solution obtained above was added thereto slowly at room temperature, and thereby to prepare an aqueous suspension. The mixing ratio of collagen to hydroxyapatite was 1:10.

The precipitate formed was filtered and freeze-dried at −20° C. until the moisture content of the precipitate became suitable for sintering. Then, this precipitate was filled into a metal container with a lid to purge air in it and sealed by welding the lid. Thereafter, the container was kept under 200 MPa at 40° C. for 8 hours.

A piece of artificial bone 22 mm in diameter and 50 mm in length was thus prepared. This artificial bone had an apparent density of 1.75 mg/ml, a Young's modulus of 2 GPa and a compression strength of 6. 5 MPa.

EXAMPLE 5

Embedding of the Artificial Bone into an Animal

A hole was made in one of the ribs of a large adult dog (German shepherd; male; body weight: 30 kg) and the artificial bone obtained in Example 5 was implanted into the hole.

Two months after this operation, the portion of bone implanted was removed and examined for inflammation and the state of assimilation. As a result, no inflammation was observed and it was found that the artificial bone implanted was functioned to osteoanagenize as the dog's bone.

EXAMPLE 6

Implantation of the artificial skin

From one of the dochizame used in Example 1, a piece of skin tissue with squama placoidea 5×5 cm was extirpated. The epidermis of the extirpated tissue was removed with the knife. The resulting tissue was immersed in saline containing 5% hypochloride for about 5 minutes to obtain rough connective tissue. The connective tissue was implanted as the artificial skin of the present invention to the dorsal of SD rats from which skin tissue was removed. Take of the grafts are observed as the same as done in Example 3.

As a result, no inflammation was observed during two months after the implantation, and the grafts were taken well to the dorsal of the hosts. Alternatively, the epidermis of the rat infiltrates into the inside of the graft from the periphery. Finally, the graft obtained from the dochizame was replaced by the rat's own skin tissue.

EXAMPLE 7

Implantation of the biomaterial substitution for muscle in allograft

The skin tissue of one dochizame in Example 1 is dissected by using a saw, and a suitable size of the muscle tissue is extirpated with the knife. The tissue was sliced in the thickness of 1 to 5 cm, and then frozen and stored in −40° C. At the time of implantation, the frozen tissue was thawed to be washed in the large volume of the sterilized saline. Then, from the washed tissue bacteria were deleted by washing in the sterilized saline containing 50 U/mL of Shiomarin. After this treatment, the tissue was implanted into femoral muscle of two dogs( both adult; body weight 30 kg and 15 kg). The take of the graft was observed after 24 hr, 48 hr, 96 hr, 7 days, 14 days, 3 month from the implantation as the same as Example 3.

As a result, no inflammation was observed, and the grafts were taken well. Furthermore, when 2 months have past from the implantation, the grafts from dochizame was replaced by the dogs' own tissues.

EXAMPLE 8

Preparation of the artificial cartilage

The aqueous calcium hydroxide ($Ca(OH)_2$) solution was prepared as the same as Example 4. On the other hand, hyaluronic acid of which weight is five % of that of hydroxyapatite and the same weight of amino acids were added to collagen-phosphate solution prepared similarly to that in Example 4 to obtain collagen-phosphate mixed solution.

The aqueous calcium hydroxide solution was then stirred vigorously, and the mixed solution was added slowly at room temperature to prepare aqueous suspension. The mixing ratio of collagen to hydroxyapatite was about 10:1(v/w).

Then, the precipitates were filtered to lyophilized until the water content in the precipitate was suitable for sintering. This precipitate was charged into a metal wear. Then the air in the wear was purged through the neck of the wear, and the neck was welded to sinter 200 MPa at about 40° C. for about 8 hours.

The artificial cartilage of which size is 22 mm in diameter×50 mm in length.

EXAMPLE 9

Implantation of the artificial cartilage of the present invention

A hole was made in femoral muscle of the large adult dog(German shepherd; male; body weight 30 kg). The artificial cartilage obtained in Example 9, which was treated similarly to that done in Example 6, was implanted into the hole.

After 24 hr, 48 hr, 96 hr, 7 days, 14 days, 3 months from the operation, the condition of the graft part was observed. No rejection was observed, and ossification was observed in the part of the implanted artificial cartilage. Accordingly, it is suggested that the artificial cartilage would function as the cartilage when it is implanted into any joint.

According to the present invention, biomedical materials comprising an extract from Chondrichthyes which are applicable to artificial bone, artificial cartilage, artificial tendon, artificial skin and surgical suture, and a method for preparing these biomedical materials are provided.

The artificial bone of the invention is obtained by sintering collagen together with hydroxyapatite under an ultrahigh pressure at a low temperature in the presence of water. Thus, it has sufficient strength to perform the functions of load supporting, etc. as well as high in biocompatibility. When the artificial bone of the invention further comprises hyaluronic acid and/or chondroitin sulfate, excellent lubricity is conferred on the artificial bone. Since the artificial bone or cartilage of the invention has a composition close to that of natural bone or cartilage, it easily adheres to the organism and undergoes remodeling.

The wound cover and artificial skin of the invention comprise Chondrichthyes-derived collagen having no antigenicity and being highly biocompatibile. Thus, they do not cause rejection nor inflammation when applied. Furthermore, since they are also superior to conventional collagen in mechanical strength, they are hard to tear, good for tightly adhering and capable of following the movement of a joint well.

Accordingly, the biomedical materials of the invention are suitable for use in the case of a severe burn, partial removal of an organ, removal of a bone or joint, or the like as a substitute for the natural counterpart. Further, the biomedical materials of the invention have an advantage that they do not leave a prominent scar when the wound has been cured.

The biomedical materials of the invention comprising a shark-derived collagen is capable of uv sterilization, high pressure sterilization and the like after final shaping.

What is claimed is:

1. A non-antigenic artificial bone or cartilage, comprising collagen from a Chondrichthyes species and hydroxyapatite, wherein the collagen is prepared by extraction and desalting without further chemical treatment to alter its antigenicity and wherein the collagen and hydroxyapatite have been sintered at a temperature below 100° C. at ultra-high pressure and is prepared by mixing a solution of about 1 to 5%(w/v) collagen with phosphate to obtain a collagen-phosphate solution, adding calcium hyroxide to the collagen-phosphate solution, and mixing the solution with hydroxyapatite powder at a ratio of about 0.1:9.9 to 2.0:8.0 to form a precipitate.

2. The non-antigenic artificial bone of claim 1, further characterized as having a bending strength greater than 700 kg/cm$^3$.

3. The non-antigenic artificial cartilage of claim 1, further comprising a component for lubrication selected from the group consisting of hyaluronic acid, chondroitin sulfate and amino acid.

4. The artificial bone or cartilage of claim 1, further characterized as an in vivo tissue culture vessel comprising both artificial cartilage and artificial bone.

5. A non-antigenic artificial bone or cartilage, comprising collagen from a Chondrichthyes species and hydroxyapatite, wherein the collagen and hydroxyapatite have been sintered at a temperature below 100° C. at ultra-high pressure, and is prepared by mixing a solution of about 1 to 5%(w/v) collagen with phosphate to obtain a collagen-phosphate solution, adding calcium hydroxide to the collagen-phosphate solution and then mixing the solution with hydroxyapatite powder at a ratio of about 0.1:9.9 to 2.0:8.0 to form a precipitate.

6. The artificial bone or cartilage of claim 5, further comprising hyaluronic acid, chondroitin sulfate, or a combination thereof.

7. A non-antigenic artificial bone or cartilage, comprising collagen from a Chondrichthyes species and hydroxyapatite, wherein the collagen is prepared by extraction and desalting without further chemical treatment to alter its antigenicity, and which is prepared by mixing a solution of about 1 to 5% (w/v) collagen with phosphate to obtain a collagen-phosphate solution, adding calcium hydroxide to the collagen-phosphate solution, mixing the solution with hydroxyapatite powder at a ratio of about 0.1:9.9 to 2.0:8.0 to form a precipitate, and then sintering the precipitate at a temperature below 100° C. at ultra-high pressure.

8. A non-antigenic artificial bone or cartilage, comprising collagen from a Chondrichthyes species and hydroxyapatite, and is prepared by mixing a solution of about 1 to 5%(w/v) collagen with phosphate to obtain a collagen-phosphate solution, adding calcium hydroxide to the collagen-phosphate solution, mixing the solution with hydroxyapatite powder at a ratio of about 0.1:9.9 to 2.0:8.0 to form a precipitate, and then sintering the precipitate at a temperature below 100° C. at ultra-high pressure.

\* \* \* \* \*